United States Patent [19]

Kollman et al.

[11] 4,198,227

[45] Apr. 15, 1980

[54] SYNERGISTIC HERBICIDAL COMPOSITIONS

[75] Inventors: Gerald E. Kollman, Chalfont; Elwood N. Irwin, Media, both of Pa.

[73] Assignee: Rohm and Haas Company, Philadelphia, Pa.

[21] Appl. No.: 547,292

[22] Filed: Feb. 5, 1975

[51] Int. Cl.² .............................................. A01N 9/02
[52] U.S. Cl. ........................................ 71/115; 71/107; 71/118; 71/124
[58] Field of Search ................................ 71/115, 124

[56] References Cited

U.S. PATENT DOCUMENTS

| | | | |
|---|---|---|---|
| 2,977,212 | 3/1961 | Tischler | 71/115 |
| 3,401,031 | 9/1968 | Inoue et al. | 71/124 |
| 3,484,230 | 12/1969 | Poignant et al. | 71/120 |
| 3,798,276 | 3/1974 | Bayer et al. | 71/124 X |

*Primary Examiner*—Catherine L. Mills
*Attorney, Agent, or Firm*—Terence P. Strobaugh

[57] ABSTRACT

Herbicidal compositions which comprise (A) 2,3,6-trichlorophenylacetic acid (fenac), or a salt, ester, or amide thereof, and (B) a diphenyl ether herbicide, exhibit synergistic activity in the control of weeds, and particularly in the control of nutsedge species.

6 Claims, No Drawings

SYNERGISTIC HERBICIDAL COMPOSITIONS

This invention relates to herbicidal compositions which comprise 2,3,6-trichlorophenylacetic acid (fenac), or an agronomically acceptable salt, ester, or amide thereof, and a diphenyl ether herbicide, and to methods of selectively controlling weeds with these compositions.

The use of selective herbicides in controlling weeds in economic crops has become an almost standard worldwide agricultural practice. However, all commercial herbicides have weaknesses against certain weeds, so that as the use of a given herbicide increases, so too does the incidence of the weed species which are not controlled by that herbicide. Consequently, many perennial plants, and in particular the nutsedges, which are not controlled by common selective herbicides have become extremely troublesome weed problems.

It has now been found that herbicidal compositions comprise 2,3,6-trichlorophenylacetic acid (fenac), or one of its agronomically acceptable salts, esters, or amides, and a diphenyl ether herbicide exhibit synergistic activity in the control of nutsedge (Cyperus) species. Generally, the fenac and the diphenyl ether in the compositions of the invention will be combined in a weight ratio of about 1:10 to about 20:1, and preferably about 1:1 to about 4:1.

A wide variety of diphenyl ether herbicides can be used in the compositions of the invention. Among the preferred classes of diphenyl ether herbicides are those containing a 2,4-dichlorophenyl ring or a 2-chloro-4-trifluoromethylphenyl ring and those containing either a 4-nitrophenyl or a 3-substituted-4-nitrophenyl ring. The most preferred diphenyl ethers are those of the formula

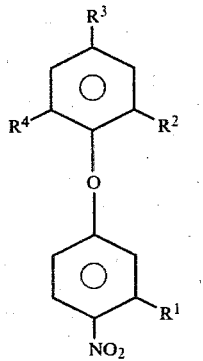

wherein
$R^1$ is a hydrogen atom, a $(C_1-C_4)$alkoxy group, preferably a methoxy or an ethoxy group, a carboxy group, a carb$(C_1-C_4)$alkoxy group, preferably a carbomethoxy or a carbethoxy group, or a carb$(C_1-C_4)$alkoxy$(C_1-C_4)$alkoxy group, preferably a carbomethoxyethoxy group or a carbethoxyethoxy group, $R^2$ is a chlorine atom or a nitro group, $R^3$ is a chlorine atom or a trifluoromethyl group, and $R^4$ is a hydrogen atom, a chlorine atom, or a fluorine atom.

Specific diphenyl ethers which can be used include 2,4-dichlorophenyl 4-nitrophenyl ether, 2-chloro-4-trifluoromethylphenyl 3-ethoxy-4-nitrophenyl ether, 2-chloro-4-trifluoromethylphenyl 3-carbomethoxy-4-nitrophenyl ether, 2-chloro-4-trifluoromethylphenyl 3-carbethoxy-4-nitrophenyl ether, 2,4,6-trichlorophenyl 4-nitrophenyl ether, 2-chloro-4-trifluoromethylphenyl 4-nitrophenyl ether, 2-nitro-4-trifluoromethylphenyl 4-nitrophenyl ether, 2,4-dichlorophenyl 3-carboxy-4-nitrophenyl ether, 2,4-dichlorophenyl 3-carbomethoxy-4-nitrophenyl ether, 2,4-dichlorophenyl 3-methoxy-4-nitrophenyl ether, 2,4-dichloro-6-fluorophenyl 4-nitrophenyl ether, 2-chloro-4-trifluoromethyl 3-(1-carbethoxy)ethoxy-4-nitrophenyl ether and the like. The first three herbicides named above are preferred.

Fenac can be used in the compositions either in its free acid form or as a suitable salt, ester, amide, or other functionally equivalent derivative. Generally, the free acid or a salt, such as the sodium salt, is preferred.

The herbicidal compositions of the invention are selective herbicides and can thus be used for the control of weeds in crops. Among the crops which are tolerant to these compositions are wheat, sugarcane, corn, barley, oats, sorghum, and the like. The compositions are effective in controlling a broad spectrum of both monocotyledonous and dicotyledonous weeds, and are particularly effective against weeds of Cyperus species, such as yellow nutsedge (Cyperus esculentus) and purple nutsedge (Cyperus rotundus). In general, the compositions are applied postemergence, that is, after the weeds have emerged from the growth medium, in a herbicidally effective amount. Generally, the compositions will be applied at a rate of about 0.25 to about 20 pounds of herbicide per acre, and preferably about 0.5 to about 10 pounds per acre.

The compositions of the invention are generally applied to the growth medium or to plants to be treated in a herbicidal formulation which also comprises an agronomically acceptable carrier. By agronomically acceptable carrier is meant any substance which can be used to dissolve, disperse, or diffuse a herbicidal compound in the composition without impairing the effectiveness of the herbicidal compound and which by itself has no detrimental effect on the soil, equipment, crops, or agronomic environment. The herbicidal compositions of the invention can be either solid or liquid formulations or solutions. For example, the compositions can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated. The two components of the compositions can be combined together in a single solution or formulation or they can be added as separate solutions or formulations to a spray tank prior to application of the mixture.

Adjuvants, such as wetting agents, spreading agents, dispersing agents, stickers, adhesives, and the like, can also be advantageously employed in accordance with agricultural practices. Examples of adjuvants which are commonly used in the art can be found in the John W. McCutcheon, Inc. publication "Detergents and Emulsifiers Annual."

The components of the herbicidal compositions of the invention can be dissolved in any appropriate solvent. Examples of solvents which are useful in the practice of this invention include alcohols, ketones, aromatic hydrocarbons, halogenated hydrocarbons, dimethylformamide, dioxane, dimethyl sulfoxide, and the like. Mixtures of these solvents can also be used. The concentration of the solution can vary from about 2% to about 98% with a preferred range being about 25% to about 75%.

For the preparation of emulsifiable concentrates, the components of the compositions can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates is usually about 10% to 60% and in flowable emulsion concentrates, this can be as high as about 75%.

Wettable powders suitable for spraying, can be prepared by admixing the components of the compositions with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to 98%, preferably about 40% to 75%. A dispersing agent can constitute about 0.5% to about 3% of the composition, and a wetting agent can constitute from about 0.1% to about 5% of the composition.

Dusts can be prepared by mixing the active components with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing about 20% to 80% of the active ingredient are commonly made and are subsequently diluted to about 1% to 10% use concentration.

Granular formulations can be prepared by impregnating a solid such as granular fuller's earth, vermiculite, ground corn cobs, seed hulls, including bran or other grain hulls, or similar material. A solution of one or both active components in a volatile organic solvent can be sprayed or mixed with the granular solid and the solvent can be sprayed or mixed with the granular solid and the solvent then removed by evaporation. The granular material can have any suitable size, with a preferable size range of 16 to 60 mesh. The active ingredient will usually comprise about 2 to 15% of the granular of the granular formulation.

The herbicidal compositions of the invention can also be mixed with fertilizers or fertilizing materials before their application. In one type of solid fertilizing composition in which the composition can be used, particles of a fertilizer or fertilizing ingredients, such as ammonium sulfate, ammonium nitrate, or ammonium phosphate, can be coated with one or more of the ethers. The compositions and solid fertilizing material can also be admixed in mixing or blending equipment, or they can be incorporated with fertilizers in granular formulations. Any relative proportion of the active ingredients and fertilizer can be used which is suitable for the crops and weeds to be treated. The total active ingredients will commonly be from about 5% to about 25% of the fertilizing composition. These compositions provide fertilizing materials which promote the rapid growth of desired plants, and at the same time control the growth of undesired plants.

The herbicidal compositions of the invention can be applied as herbicidal sprays by methods commonly employed, such as conventional high-gallonage hydraulic sprays, low-gallonage sprays, airblast spray, aerial sprays and dusts. For low volume applications a solution of the active components is usually used. The dilution and rate of application will usually depend upon such factors as the type of equipment employed, the method of application, the area to be treated and the type and stage of development of the weeds.

The following examples will further illustrate this invention but are not intended to limit it in any way. A greenhouse method is used to show the increased weed control of the combination of fenac or its salts with diphenyl ether herbicides over that which would be predicted from the herbicidal activities of the individual components alone. The following diphenyl ether herbicides were used in combination with fenac (as its sodium salt):

(I) 2,4-dichlorophenyl 4-nitrophenyl ether
(II) 2-chloro-4-trifluoromethylphenyl 3-ethoxy-4-nitrophenyl ether
(III) 2-chloro-4-trifluoromethylphenyl 3-carbomethoxy-4-nitrophenyl ether
(IV) 2-chloro-4-trifluoromethylphenyl 3-(1-carbethoxy)ethoxy-4-nitrophenyl ether
(V) 2,4-dichlorophenyl 3-carbomethoxy-4-nitrophenyl ether
(VI) 4-chloro-2-nitrophenyl 4-nitrophenyl ether
(VII) 2,4,6-trichlorophenyl 4-nitrophenyl ether The following test procedure is employed. Seeds or nutlets of selected species are planted in soil in flats. The seeds are allowed to germinate, and after two weeks the flats are treated with the test compounds and compositions. The compounds and mixtures to be evaluated are dissolved in acetone or water, and sprayed over the flats using a carrier volume equivalent to 50 gallons per acre at the rate of application (pounds per acre, lb./A.) specified in the tables. About two weeks or about four weeks after the application of the test compound or composition, the state of growth of the plants is observed and the phytotoxic effect of the compound is evaluated. Tables I to III give the average percent control achieved by the test compounds in terms of the percent of the plants which are killed by the compounds. (--) indicates that the test was not carried out at the noted rates.

TABLE I

ACTIVITY AGAINST YELLOW NUTSEDGE (*Cyperus esculentus*)
(% Control-two weeks after treatment)

| Ether | (lb./A) | Fenac (lb./A) | | | | | |
|---|---|---|---|---|---|---|---|
| | | 0 | ¼ | ½ | 1 | 2 | 4 |
| I | 0 | 0 | 0 | 0 | 10 | 0 | 20 |
| I | 1 | 40 | 70 | 70 | 70 | 90 | — |
| I | 2 | 50 | 60 | 70 | 70 | 99 | — |
| I | 4 | 50 | 60 | 90 | 95 | 99 | — |
| I | 8 | 60 | — | — | — | — | — |
| II | 0 | 0 | — | — | 0 | 10 | 40 |
| II | ¼ | 15 | — | — | 78 | 93 | — |

TABLE I-continued

ACTIVITY AGAINST YELLOW NUTSEDGE (*Cyperus esculentus*)
(% Control-two weeks after treatment)

| Ether | (lb./A) | Fenac (lb./A) | | | | | |
|---|---|---|---|---|---|---|---|
| | | 0 | 1/4 | 1/2 | 1 | 2 | 4 |
| II | 1/4 | 45 | — | — | 88 | 97 | — |
| II | 1/2 | 50 | — | — | 93 | 99 | — |
| II | 1 | 75 | — | — | — | — | — |
| III | 0 | 0 | — | — | 0 | 10 | 40 |
| III | 1/8 | 20 | — | — | 80 | 95 | — |
| III | 1/4 | 45 | — | — | 99 | 95 | — |
| III | 1/2 | 50 | — | — | 90 | 100 | — |
| III | 1 | 78 | — | — | — | — | — |

TABLE II

ACTIVITY AGAINST YELLOW NUTSEDGE (*Cyperus esculentus*)
(% Control-four weeks after treatment)

| Ether | (lb./A) | Fenac (lb./A) | | | |
|---|---|---|---|---|---|
| | | 0 | 1 | 2 | 4 |
| II | 0 | 0 | 10 | 15 | 25 |
| II | 1/8 | 10 | 80 | 100 | — |
| II | 1/4 | 30 | 99 | 100 | — |
| II | 1/2 | 40 | 100 | 100 | — |
| II | 1 | 65 | — | — | — |
| III | 0 | 0 | 10 | 15 | 25 |
| III | 1/8 | 30 | 95 | 95 | — |
| III | 1/4 | 25 | 99 | 99 | — |
| III | 1/2 | 60 | 85 | 100 | — |
| III | 1 | 85 | — | — | — |
| IV | 0 | 0 | — | 20 | 30 |
| IV | 1/4 | 65 | — | 100 | — |
| IV | 1/2 | 100 | — | — | — |
| V | 0 | 0 | — | 20 | 30 |
| V | 2 | 65 | — | 80 | — |
| V | 4 | 30 | — | — | — |
| VI | 0 | 0 | — | 20 | 30 |
| VI | 2 | 20 | — | 95 | — |
| VI | 4 | 25 | — | — | — |
| VII | 0 | 0 | — | 20 | 30 |
| VII | 2 | 5 | — | 90 | — |
| VII | 4 | 25 | — | — | — |

TABLE III

ACTIVITY AGAINST PURPLE NUTSEDGE (*Cyperus rotundus*)
(% Control-two weeks after treatment)

| Ether | (lb./A) | Fenac (lb./A) | | | | | |
|---|---|---|---|---|---|---|---|
| | | 0 | 1/4 | 1/2 | 1 | 2 | 4 |
| I | 0 | 0 | 0 | 0 | 0 | 10 | 20 |
| I | 1 | 0 | 20 | 20 | 30 | 30 | — |
| I | 2 | 30 | 40 | 50 | 90 | 80 | — |
| I | 4 | 40 | 50 | 60 | 70 | 80 | — |
| I | 8 | 50 | — | — | — | — | — |

The above data demonstrates the unexpected synergistic activity of herbicidal compositions comprising fenac and a diphenyl ether herbicide, when compared to the individual activity of the components of the compositions.

It is to be understood that changes and variations may be made without departing from the spirit and scope of the invention as defined by the appended claims.

We claim:

1. A synergistic herbicidal composition comprising (A) 2,3,6-trichlorophenylacetic acid, or an agronomically acceptable salt, ester, or amide thereof, and (B) 2-chloro-4-trifluoromethylphenyl-3-ethoxy-4-nitrophenyl ether wherein the weight ratio of (A) to (B) is about 1:1 to about 4:1.

2. A synergistic herbicidal composition comprising (A) 2,3,6-trichlorophenylacetic acid, or an agronomically acceptable salt, ester, or amide thereof, and (B) 2-chloro-4-trifluoromethylphenyl-3-carbomethoxy-4-nitrophenyl ether wherein the weight ratio of (A) to (B) is about 1:1 to about 4:1.

3. A composition of claims 1 or 2 which additionally comprises agronomically-acceptable carrier and a surfactant.

4. A method of controlling weeds which comprises applying to the weeds a composition according to claim 1 or 2 in a herbicidally effective amount.

5. The method of claim 4 wherein the composition is applied at a rate of about 0.25 to about 20 pounds per acre of the composition.

6. The method of claim 5 wherein the weeds are Cyperus species.

* * * * *